(12) United States Patent
Grubbs et al.

(10) Patent No.: US 6,376,690 B1
(45) Date of Patent: Apr. 23, 2002

(54) METHOD OF REMOVING TRANSITION METALS

(75) Inventors: Robert H. Grubbs; Heather D. Maynard, both of Pasadena, CA (US); David M. Lynn, Somerville, MA (US)

(73) Assignee: California Institute O Technology, Pasadena, CA (US)

( * ) Notice: Subject to any disclaimer, the term of this patent is extended or adjusted under 35 U.S.C. 154(b) by 0 days.

(21) Appl. No.: 09/386,205

(22) Filed: Aug. 30, 1999

Related U.S. Application Data

(60) Provisional application No. 60/099,592, filed on Sep. 9, 1998.

(51) Int. Cl.$^7$ .............................. C07F 15/00; C07F 9/28

(52) U.S. Cl. ......................................... 556/21; 556/136

(58) Field of Search ................................... 556/21, 136

(56) References Cited

U.S. PATENT DOCUMENTS

| | | | |
|---|---|---|---|
| 5,342,909 A | 8/1994 | Grubbs et al. | ............... 526/171 |
| 5,710,298 A | 1/1998 | Grubbs et al. | ................. 556/22 |
| 5,728,917 A | 3/1998 | Grubbs et al. | ............... 585/653 |
| 5,831,108 A | 11/1998 | Grubbs et al. | ................. 556/21 |

OTHER PUBLICATIONS

Webster's Ninth New Collegiate Dictionary, Merriam–Webster Inc., Publishers, Springfield, Massachusetts, pp. 997 and 1073, 1990.*

Maynard, H.D., et al., "Purification Technique for the Removal of Ruthenium from Olefin Metathesis Reaction Products," Tetrahedron Letters, 40, (1999), pp. 4137–4140.

Schwab, P., et al., "Synthesis and Applications of $RuCl_2$(=CHR ')$(PR_3)_2$: The Influence of the Alkylidene Moiety on Metathesis Activity," J. Am. Chem. Soc., vol. 118, No. 1, (1996), pp. 100–110.

Schwab, P., et al., "A Series of Well–Defined Metathesis Catalysts–Synthesis of [RuCl(=CHR')$(PR_3)_2$)] and Its Reactions," Angew. Chem. Int. Ed. Engl. (1995), 34, No. 18, pp. 2039–2041.

Ivin, K.J., "Some recent applications of olefin metathesis in organic synthesis: A review," Elsevier, Journal of Molecular Catalysis A: Chemical 133, (1998), pp. 1–16.

Schuster, M., et al., "Olefin Metathesis in Organic Chemistry," Angew. Chem, Int. Ed. Engl. (1997), 36, pp. 2037–2056.

Grubbs, R.H., et al., "Recent Advances in Olefin Metathesis and Its Application in Organic Synthesis," Tetrahedron 54, (1998), pp. 4413–4450.

Ellis, J.W., et al., "Water–Soluble Tris(hydroxymethyl)phosphine Complexes with Nickel, Palladium, and Platinum. Crystal Structure of $[Pd\{P(CH_2OH)_3\}_4]\cdot CH_3OH$," Inorg. Chem. (1992), 31, pp. 3026–3033.

Hoye, P.A.T., et al., "Hydrophosphination of Formaldehyde catalysed by Tris–(hydroxymethyl)phosphine Complexes of Platinum, Palladium or Nickel," J. Chem. Soc. Dalton Trans., (1993), pp. 269–274.

Berning, D.E., et al., "Multifaceted Reactions of $P(CH_2OH)_3$ with Rhenium(V) Precursors. Synthesis, Characterization, and X–ray Structural Studies of trans,trans,trans—$[ReO_2\{P(CH_2OH)_3\}_2-(py)_2]Cl$, trans,cis,cis–$[ReO_2\{P(CH_2OH)_3\}_2(py)_2]Ci$, and Novel Alkoxide $[Re(O)(\mu-\eta^2-P\{CH_2OH\}_2CH_2O]_4$," Inorg. Chem., (1998), 37, pp. 334–339.

Goodwin, N.J., et al., "Synthesis and reactivity of the foerrocene–derived phosphine $[Fe(\eta-C_5H_5)-\{\eta-C_5H_4CH_2P(CH_2OH)_2\}]$," J. Chem. Soc., Dalton Trans., (1997), pp. 4377–4384.

Komiya, S., et al, "Synthesis of water–soluble (tri(hydroxymethyl)phosphine)gold(I) complexes containing a nucleoside ligand," Inorganica Chimica Acta, 217, (1994), pp. 201–202.

Berning, D.E., et al., "In Vitro and In Vivo Characterization of a $^{99m}$Tc complex with Tris(hydroxymethyl)phosphine (THP)," Nuclear Medicine & Biology, vol. 23, (1996), pp. 617–622.

Berning, D.E., et al., "Hydroxymethyl Functionalized Phosphanes as Building Blocks to New Water–Soluble Gold(I) Complexes—Synthesis, Characterization, and X–ray Crystal Structures of Novel Tetrahedral $[Au\{P(CH_2OH)_3\}_4]^+$ and Trigonal Planar $[au(Ph_2PCH_2OH)_3]^+$ Gold(I) Complexes," Chemistry in Environmentally Benign Media, 8, (1997), pp. 907–911.

Higham, L., et al., "Formation and X–ray structure of a novel water–soluble tertiary–secondary phosphine complex of ruthenium(II): $[Ru\{P(CH_2OH)_3\}_2\{P(CH_2OH)_2H\}_2Cl_2]$," Chem. Commun., (1998), pp. 1107–1108.

(List continued on next page.)

Primary Examiner—Porfirio Nazario-Gonzalez
(74) Attorney, Agent, or Firm—Pillsbury Winthrop LLP; Tanuja V. Garde

(57) ABSTRACT

The present invention generally relates to the discovery that the solubility of metal complexes may be readily manipulated by the addition of one or more solubility-enhancing compounds. This manipulation of the solubilities allows for the preparation of suitable samples for precise quantitative analysis and for the facile purification of the desired products from the reaction mixture containing one or more metal complexes. In one embodiment of the invention, the relative solubilities between two solutions are manipulated so as cause the metal complex found in a first solution to transfer to a second solution that is generally immiscible with the first solution. The metal complex is thus separated from the reaction mixture which comprises the first solution by the removal of the second solution. In another embodiment, the solubility-enhancing compounds of the present invention is used to prepare samples containing metal complexes for precise quantitative analysis such as inductively coupled plasma mass spectroscopy.

26 Claims, 1 Drawing Sheet

OTHER PUBLICATIONS

Drießen–Hölscher, B., et al., "Selective two–phase–hydrogenation of sorbic acid with novel water soluble ruthenium complexes," Elsevier Science S.A., (1998), pp. 141–146.

Kirkland, T.A., "Effects of Olefin Substitution on the Ring–Closing Metathesis of Dienes," J. Org. Chem., (1997), 62, pp. 7310–7318.

Shido, T., et al., "$Rh_4$ Carbonyl Clusters Coordinated with Tris(Hydroxymethyl)phosphine Grafted onto $SiO_2$ Surfaces and Structural Control of Active Sites in Gas–Phase Olefin Hydroformylation Reactions," Journal of Catalysis, (1995), 157, pp. 436–449.

Marsella, M.J., et al., "Template–Directed Ring–Closing Metathesis: Synthesis and Polymerization of Unsaturated Crown Ether Analogs," Angew. Chem. Int. Ed Engl., (1997), 36, No. 10, pp. 1101–1103.

* cited by examiner

METHOD OF REMOVING TRANSITION METALS

This application claims the benefit of U.S. Provisional Application No. 60/099,592, filed Sep. 9, 1998 by inventors Robert H. Grubbs, Heather D. Maynard, and David M. Lynn entitled METHOD OF REMOVING TRANSITION METALS which is incorporated herein by reference in its entirety.

The U.S. Government has certain rights in this invention pursuant to Grant No. GM 31332 awarded by the National Institute of Health.

BACKGROUND

Despite the ubiquitous use of metal complexes in organic reactions, a simple method for their removal has yet to be discovered. Unfortunately, residual metals often must be removed from the reaction mixture because they can interfere with subsequent transformations and can pose problems for shelf-life and use of the final product.

Current methods for removing metal complexes involve running the reactant mixture through numerous columns or other similarly rigorous purification strategies. In addition to being cumbersome, these procedures are time consuming and labor intensive. As uses for metal complexes increases, a simple and facile method for their removal is increasingly needed and desired.

SUMMARY OF THE INVENTION

The present invention generally relates to the discovery that the solubility of metal complexes may be readily manipulated by the addition of one or more solubility-enhancing compounds. In one embodiment of the present invention, the solubility-enhancing compounds are used to prepare samples containing metal complexes for precise quantitative analysis such as inductively coupled plasma mass spectroscopy ("ICP-MS"). In one embodiment of the invention, the relative solubilities between two solutions are manipulated so as cause the metal complex in a first solution (typically the reaction mixture) to transfer into a second solution that is generally immiscible with the first solution. The removal of the second solution thus also removes the metal complex from the reaction mixture. This embodiment is particularly useful for separating the metal complex from the reaction product.

DETAILED DESCRIPTION OF THE INVENTION

Figure 1:
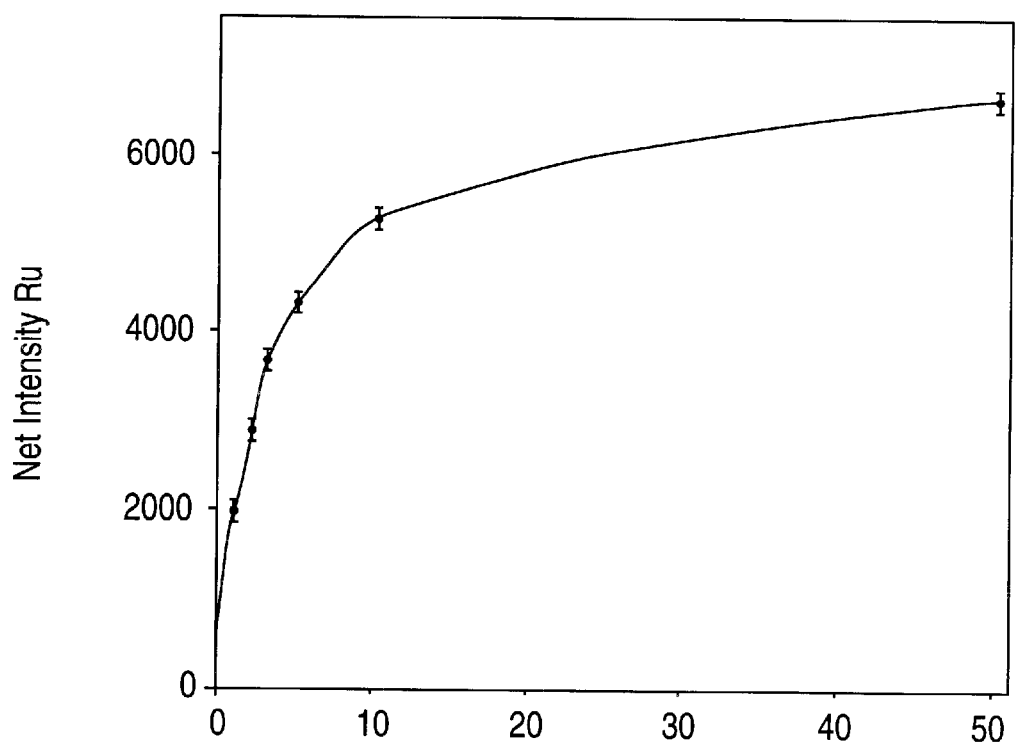
FIG. 1 displays the net intensity of the ruthenium signal from the aqueous phase versus the number of equivalents of the solubility-enhancing compound (2) used.

The present invention generally relates to the discovery that the solubility of metal complexes may be readily manipulated by the addition of one or more solubility-enhancing compounds. This manipulation of the solubilities allows for the preparation of suitable samples for precise quantitative analysis and for the facile purification of the desired products from the reaction mixture containing one or more metal complexes.

In the most general sense, the present invention relates to a method of enhancing the solubility of a metal complex (or a combination of metal complexes) in a solution by the addition of one or more solubility-enhancing compounds to the solution.

As used herein, the term "metal complexes" include the metal compound itself (e.g. Cu, Mg, Ru, Os, etc), its ions, and metal containing or metal associated compounds (either through covalent bounds or through other intermolecular forces such as chelation). Illustrative examples of metal complexes whose solubilities may be manipulated through the practice of the present invention include but are not limited to complexes of: cadmium, chromium, cobalt, copper, gold, iridium, iron, magnesium, manganese, mercury, molybdenum, nickel, osmium, palladium, platinum, rhenium, rhodium, ruthenium, silver, technetium, tungsten, and zinc.

As used herein, "solubility-enhancing compounds" are compounds that interact with a metal complex in a manner that enhances the solubility of the complex in the desired solution. Suitable examples of solubility-enhancing compounds include but are not limited to: phosphines, sulfonated phosphines, phosphites, phosphinites, phosphonites, arsines, stibines, ethers, amines, amides, imines, sulfoxides, carboxyls, nitrosyls, pyridines, and thioethers.

In preferred embodiments, the solubility-enhancing compound is of the general formula $PR^1R^2R^3$ wherein $R^1$, $R^2$, and $R^3$ are each independently selected from a group consisting of hydrogen, aryl, heteroaryl, $C_1-C_{10}$ alkyl, and cycloalkyl groups, each optionally substituted with one or more substituents selected from the group consisting of $C_1-C_5$ alky, $C_2-C_5$ alkenyl, $C_2-C_5$ alkynyl, allyl, aryl, and heteroaryl. The term "alkyl" includes primary alkyl, secondary alkyl, and tertiary alkyl. The solubility-enhancing compound $PR^1R^2R^3$ may also include one or more functional groups selected from the group consisting of: alcohol, sulfonic acid, phosphine, phosphonate, phosphonic acid, thiol, ketone, aldehyde, ester, ether, amine, quaternary ammonium, imine, amide, imide, imido, nitro, carboxylic acid, disulfide, carbonate, isocyanate, carbodiimide, carboalkoxy, carbamate, acetal, ketal, boronate, cyanohydrin, hydrazone, oxime, oxazole, oxazoline, oxalane, hydrazide, enamine, sulfone, sulfide, sulfenyl, and halogen.

The choice of a particular solubility-enhancing compound will depend on the chemical properties of metal complex and of the solution in which the solubility of the metal complex is to be enhanced. For example, if the solubility of the metal compound is to be enhanced in an aqueous solution, then compounds of the formula $PR^1R^2R^3$ that are soluble in aqueous solution are selected. Illustrative examples of such solubility-enhancing compounds include but are not limited to: $P(CH_2OH)_3$; $P(PhSO_3Na^+)$; $(CH_2OH)_2P—P(CH_2OH)_2$; and $P(CyOH)_3$ wherein Ph is phenyl and Cy is cyclohexyl. Similarly, if the solubility of the metal complex is to be enhanced in an organic solution, then compounds of the formula $PR^1R^2R^3$ that are soluble in organic solution are selected. Illustrative examples of such solubility-enhancing compounds include but are not limited to: $P(Cy)_3$, $PH(Cy)_2$; $P(Ph)_3$; and $P(R)_3$ wherein Ph is phenyl, Cy is cyclohexyl, and R is $C_1-C_5$ alkyl (primary, secondary or tertiary).

In general, the solubility-enhancing compounds of the present invention are used alone. However, when the particular solubility-enhancing compound is not sufficiently pure (<85%), then the efficiency and effectiveness of these compounds have been found to substantially increase with the addition of either a base or an acid (depending on the functionalities found on the particular solubility-enhancing compound). For example, some commercial preparations of tris(hydroxylnethyl)phosphine may include the hemiacetal form of the compound. The addition of a base will reverses the formation of the hemiacetal in organic solutions. As a result, it has been found that the addition of a base such as triethylamine will enhance the performance of less pure preparations of tris(hydroxylmethyl)phosphine in solubilizing metal complexes, particular ruthenium complexes, in organic solutions. The resulting tris(hydroxylmethyl) phosphine-ruthenium complex is also now much more soluble in aqueous solution and if an aqueous phase were added to the organic phase, it would preferentially migrate to the aqueous phase.

In one embodiment of the present invention, the use of the solubility-enhancing compounds is used to prepare samples containing metals or metal complexes for precise quantitative analysis. For example, inductively coupled plasma mass spectrometry ("ICP-MS") is an instrument that is capable of detecting metals on the order of parts per million to parts per trillion. Unfortunately, because ICP-MS requires an aqueous sample, the utility of this instrument has been limited by the time consuming and laborious procedures that are required to prepare samples of metal complexes that are not generally soluble in aqueous solutions. With the practice of the present invention, samples of most metal complexes may be readily prepared. In another example, the inventive methods may be used to prepare samples of metal complexes for atomic absorption.

In another aspect of the present invention, the manipulation of the solubilities allows for the facile purification of the desired products from the reaction mixture containing one or more metal complexes. In general, the method involves combining a first solution (typically the reaction mixture containing the desired product and one or metal complexes) with a second solution wherein the second solution is immiscible with the first solution;

adding a solubility-enhancing compound that enhances the solubility of the metal complex in the second solution;

mixing the first solution with the second solution together; and removing the second solution from the first solution.

Because the first solution and the second solution are immiscible with each other, it is immaterial whether the first solution is added to the second solution or vice versa. Moreover, the solubility-enhancing compound may be added to the first solution or the second solution or to the combined solutions so long as it is present prior to the mixing of the first solution with the second solution. However, it is preferred that the solubility-enhancing compound is added to the first solution prior to the combining of the first solution with the second solution.

The identities of the solubility-enhancing compound and the second solution will depend on the nature of the reaction (including identity of the metal complex) and whether the reaction takes place in an aqueous or organic solution. For example, if the transformation requiring a metal complex occurs in an organic solution, then solubility-enhancing compounds that would preferentially enhance the solubility of the metal complex in aqueous solutions are chosen. Similarly, if the transformation requiring a metal complex occurs in aqueous solution, then solubility-enhancing compounds that would preferentially enhance the solubility of the metal complex in organic solutions are chosen. It should be noted that in some cases, the solubility-enhancing compound may enhance the solubility of the metal complex in both aqueous and organic (first and second) solutions. However, because the solubility-enhancing compound is chosen so that metal complex is made to be much more soluble in the second solution than in the first solution, the metal complex will migrate into the second solution from the first solution (typically the reaction mixture) upon the mixing (by shaking, stirring, or otherwise) of the first solution with the second solution. As a result, the metal complex may be removed from the reaction mixture (and thus from the product of interest), by the removal of the second solution which is immiscible with the reaction mixture. In preferred embodiments wherein the reaction takes place in an organic solution, the method further comprises adding an acid or a base prior to the mixing of the first solution with the second solution. Like the solubility-enhancing compound, the acid/base may be added to the first solution or the second solution or to the combined solutions so long as it is present prior to the mixing of the first solution with the second solution.

In a variation of the above method, silica gel may be used instead of the second solution. The method comprises adding a solubility-enhancing compound to a solution containing a metal complex;

adding silica gel to the solution; and, removing the silica gel from the solution.

This method is particularly effective for removing metal complexes in RCM and ROMP reactions. Silica gel is sometimes referred to as silica or silicon dioxide and essentially consists of $SiO_2$. Any pore size of $SiO_2$ may be used. Illustrative examples of commercially available silica gels suitable for the practice of the present invention include materials sold under the trade names of Aerosil and Cabosil. Optionally, the method may further comprise adding an acid or a base to the solution. In the case of ROMP reactions, it is preferred to heat the solution comprising the solubility-enhancing compound and silica gel prior to removing the silica gel from the solution. In even more preferred embodiments, the solution is heated to approximately 40° C. for between about 1 to about 3 hours prior to removing the silica gel. In another variation of the same theme, the solubility-enhancing compound may be grafted onto the silica gel and thus would eliminate the need for adding a separate solubility-enhancing compound to the solution.

In another variation of the above method, the first solution (typically the reaction mixture containing both the product of interest and the metal complex) and second solution are miscible but the desired product is insoluble in the second solution. In general, the method comprises adding a solubility-enhancing compound that enhances the solubility of the metal complex in the second solution;

combining the first solution with the second solution to form a mixture;

precipitating the reaction product from the mixture; and removing the reaction product precipitate from the mixture.

As with prior embodiments, the solubility-enhancing compound may be added to the first solution or the second solution, or the combined solutions. However, it is generally preferred that the solubility-enhancing compound is added to the first solution prior to the combining of the first solution with the second solution.

Practice of this embodiment is particularly useful in purifying the product polymers of ring-opening metathesis polymerization ("ROMP") reactions. The reaction is generally carried out in the reaction medium (the first solution). Once polymerization is complete, the product is precipitated out of the reaction medium by dripping the reaction medium into a second solution in which the ROMP polymer product is insoluble. In general, it is preferred that the first solution contains the solubility-enhancing compound prior to being dripped into the second solution. Alternatively, the second solution may be dripped into the reaction medium. In either case, because the solubility of the metal complex has been enhanced in the second solution, it will preferentially remain in the second solution and the precipitated polymer will be substantially free of the metal complex.

The inventive methods are generally application and may be used, for example, to remove Ni and Pd catalysts from polymers made for photoresist materials where it is imperative that the metal be removed completely for the final application. However, practice of the present invention is especially amenable for the post-reaction separation of ruthenium and osmium metathesis catalysts from the desired products. Illustrative embodiments of these catalysts have been described, for example, by U.S. Pat. Nos. 5,342,940, 5,849,851, 5,831,108, and 5,917,071 (which are all incorporated herein by reference). These catalysts are incredibly versatile and have been used in a variety of metathesis reactions including ring-opening metathesis polymerization ("ROMP") reactions, ring-closing metathesis ("RCM") reactions, self and cross-metathesis reactions, depolymerization of unsaturated polymers, synthesis of telechelic polymers, and acyclic diene metathesis polymerization ("ADMET") reactions. Briefly, the catalysts are of the general formula

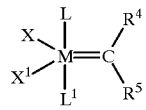

wherein:
M is ruthenium or osmium;
X and $X^1$ are each independently any anionic ligand;
L and $L^1$ are each independently any neutral electron donor ligand;
$R^4$ and $R^5$ are each independently hydrogen or a substituent selected from the group consisting of $C_1$–$C_{20}$ alkyl, $C_2$–$C_{20}$ alkenyl, $C_2$–$C_{20}$ alkeynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the $R^4$ or $R^5$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In preferred embodiments of these catalysts, the $R^4$ substituent is hydrogen and the $R^5$ substituent is selected from the group consisting of $C_1$–$C_{20}$ alkyl, $C_2$–$C_{20}$ alkenyl, and aryl. In even more preferred embodiments, the $R^5$ substituent is phenyl or vinyl, optionally substituted with one or more moieties selected from the group consisting of $C_1$–$C_5$ alkyl, $C_1$–$C_5$ alkoxy, phenyl, and a functional group. In the most preferred embodiments, the $R^1$ substituent is phenyl or —C=C(CH$_3$)$_2$.

In preferred embodiments of these catalysts, L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. In more preferred embodiments, L and $L^1$ are each a phosphine of the formula PR$^6$R$^7$R$^8$, where $R^6$, $R^7$, and $R^8$ are each independently aryl or $C_1$–$C_{10}$ alkyl, particularly primary alkyl, secondary alkyl or cycloalkyl. In the most preferred embodiments, L and $L^1$ ligands are each selected from the group consisting of -P(cyclohexyl)$_3$, -P(cyclopentyl)$_3$, -P(isopropyl)$_3$, and -P(phenyl)$_3$.

In preferred embodiments of these catalysts, X and $X^1$ are each independently hydrogen, halide, or one of the following groups: $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, or $C_1$–$C_{20}$ alkylsulfinyl. Optionally, X and $X^1$ may be substituted with one or more moieties selected from the group consisting of $C_1$–$C_{10}$ alkyl, $C_1$–$C_{10}$ alkoxy, and aryl which in turn may each be further substituted with one or more groups selected from halogen, $C_1$–$C_5$ alkyl, $C_1$–$C_5$ alkoxy, and phenyl. In more preferred embodiments, X and $X^1$ are halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate. In even more preferred embodiments, X and $X^1$ are each halide, CF$_3$CO$_2$, CH$_3$CO$_2$, CFH$_2$CO$_2$, (CH$_3$)$_3$CO, (CF$_3$)$_2$(CH$_3$)CO, (CFO$_3$)(CH$_3$)$_2$ CO, PhO, MeO, EtO, tosylate, mesylate, or trifluoromethanesulfonate. In the most preferred embodiments, X and $X^1$ are each chloride.

Scheme 1 illustrates the practice of the present invention with reference the use and removal of compound 1 using an especially preferred embodiment of the solubility-enhancing compound, tris(hydroxymethyl)phosphine (compound 2).

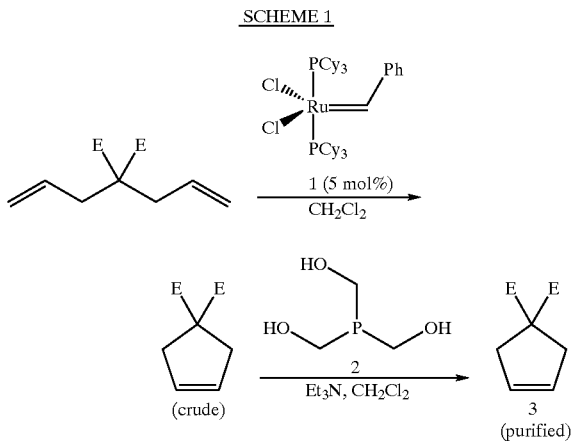

As indicated, diethyl diallylmalonate was ring-closed using compound 1 to form compound 3. Tris (hydroxylmethyl)phosphine 2 was added to the reaction mixture and following aqueous extraction, the residual ruthenium was quantified by ICP-MS. Table 1 shows the results of a series of purification experiments.

TABLE 1

| Entry | Method | Amount of Ruthenium (μg/5 mg product) |
|---|---|---|
| 1 | crude | 74.6 ± 0.8 |
| 2 | 86 eq., 2, 1 H$_2$O wash | 5.72 ± 0.07 |
| 3 | 378 eq., 2, 1 H$_2$O wash | 8.84 ± 0.07 |
| 4 | 86 eq., 2, 3 H$_2$O washes | 3.35 ± 0.07 |
| 5 | 86 eq., 2, 1 H$_2$O wash, repeated 3 times | 3.56 ± 0.07 |
| 6 | 86 eq., 2, stir with silica gel, filter | 1.03 ± 0.04 |

*Number of eq. of 2 based on the amount of 1 added. In each case 3 eq. of Et$_3$N was used.

As shown by Table 1, all purification methods achieved a more than 10-fold decrease in the amount of ruthenium remaining in the sample compared to the crude sample (entry 1). The results were similar whether 86 equivalents (entry 2) or 378 equivalents (entry 3) of tris(hydroxymethyl)phosphine were used followed by one aqueous wash. The amount of ruthenium in the product could be decreased by adding 86 equivalents of tris(hydroxymethyl)phosphine followed by 3 aqueous washes (entry 4) or adding tris(hydroxymethyl)phosphine to the methylene chloride layer three times followed by an aqueous wash each time (entry 5). Because tris(hydroxymethyl)phosphine is polar and is known to graft onto silica gel, a purification by stirring a solution of product, tris(hydroxymethyl)phosphine, and triethylamine in methylene chloride with an excess of silica gel (entry 6) was attempted. This method gave the best results and the amount of residual ruthenium remaining in the sample was reduced to 1 μg in 5 mg of product.

Next, a series of experiments were undertaken to study the minimum amount of tris(hydroxymethyl)phosphine that would be necessary to draw ruthenium into the aqueous phase. FIG. 1 is a graphical representation of the net ICP-MS intensity of ruthenium in the aqueous phase after adding a certain number of equivalents of tris(hydroxymethyl)phosphine to the methylene chloride layer followed by a H$_2$O wash. Although as little as one equivalent of tris(hydroxymethyl)phosphine was sufficient to dramatically decrease the amount of ruthenium in the product contained in the organic layer, about ten equivalents were needed to efficiently extract the ruthenium into the aqueous layer from the methylene chloride phase.

Another example of the practice of the present invention is the RCM reaction of bisallyl triethylene glycol with a ruthenium metathesis catalyst, such as compound 1, which yields crown ether 4. Compound 4 is of interest because it may be polymerized by ROMP to yield a commercially useful polyether. Unfortunately, during the distillation purification of 4, the residual ruthenium from the reaction causes about 2–5% of 4 to be isomerized into 5. This isomerization reaction is illustrated by Scheme 2.

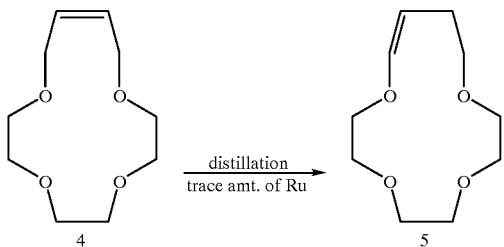

Because the isomerization product 5 tends to inhibit the further ROMP reaction of 4, the separation of ruthenium from the RCM product 4 presented a good example of the utility of the present invention.

When 4 was pretreated with tris(hydroxymethyl)phosphine and purified with one aqueous wash, the ruthenium concentration was reduced from 80 to 8.8 gg per 5 μg of 4 as determined by ICP-MS. Since this decrease in the ruthenium concentration was sufficient to inhibit the detrimental isomerization during distillation, further purification of ruthenium from 4 was not necessary.

In another embodiment of the present invention, the solubility-enhancing compound is built into the metal complex. Using the above-described ruthenium and osmium metathesis catalysts as an example, L and/or L$^1$ are modified to include one or more protected functional groups that may be subsequently exposed after the desired organic transformation. The identity of the protected functional group depends on whether the catalyst's solubility in aqueous or organic solvent is being enhanced.

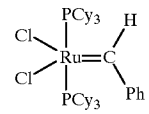

Using compound 1 as an example (wherein Cy is cyclohexyl), if enhanced solubility in aqueous solution of this catalyst is desired, the cyclohexyl group may be modified to CyCOOR$^9$ wherein R$^9$ is as described above for R$^1$, R$^2$ and R$^3$. These modified catalysts may be used as previously described. However, after the desired reaction, the ester moieties may be cleaved to expose the carboxyl fictional groups. This transformed catalyst will now be substantially more soluble in aqueous solution relative to organic solution so that it may be readily separated from the products of the catalyzed reaction. This strategy may be readily generalized to modulate the post-reaction solubilities of other embodiments of the previously described ruthenium and osmium catalysts.

In another variation of the transformed catalyst scenario, the ruthenium and osmium catalysts may be used as described but the catalyst is subsequently modified as a final step in the metathesis reaction. For example, in a ring-opening metathesis polymerization ("ROMP") reaction, compound 1 would be attached to the growing ROMP polymer product during the propagation step. When the polymer product reached the desired size, a transforming compound is added to the mixture that reacts with the metal complex in the regeneration step in such a manner as to alter the solubility characteristic of the metal complex. Although the term "transforming compound" is used emphasize the mechanism of this particular embodiment, transforming compounds are simply a subset of solubility-enhancing compounds that have been described above. In other words, transforming compounds also enhances the solubility of the metal complex in the desired solution.

Scheme 3 is an illustration of this embodiment. The transformed metal complex, (Cl)$_2$(PCy$_3$)$_2$Ru=COR, will be preferentially soluble in the precipitating solvent. Thus, when the polymer product is precipitated out of solution, the metal complex will remain behind.

SCHEME 3

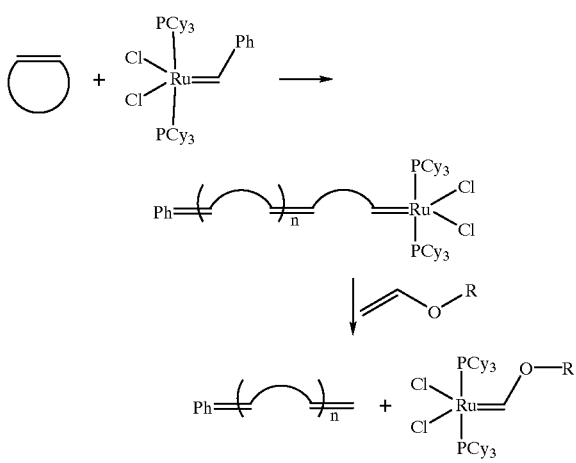

In this example, CH₂CHOR is the transforming compound. When the ROMP polymer product is non-polar, the R group will be polar so that the solubility of the transformed metal complex will be enhanced in the precipitating generally polar solution (i.e., methanol). Similarly, when the ROMP polymer product is polar, then the R group will be typically non-polar so that the solubility of the transformed metal complex will be enhanced in the precipitating generally non-polar solution (i.e., hexane).

Although the present invention has been described with examples and references to preferred embodiments, it should be appreciated that the above descriptions were for the purposes of illustration only and not intended in any way to limit the scope of the present invention. For example, the solubility-enhancing compounds may be bound to solid support (i.e., polymers, silica, etc.) and used to extract the metal complexes as a solution containing said metal complexes is filtered or passed therethrough.

EXPERIMENTAL SECTION

Ring-Closing Metathesis

Diethyl diallymalonate (0.414 mmol) was added to a Schlenk flask equipped with a stir bar. The flask was purged with argon and vacuum pumped 5 times. Dichloromethane (18.7 ml) was added to the flask and compound 1 was added in 2 ml of CH₂Cl₂. The final concentration of the substrate was 0.02 M. The reaction mixture was vigorously stirred at room temperature for 2 hours and 15 minutes and then ethyl vinyl ether (0.1 M) was added. Equivalent aliquots of the resulting solution equaling 0.1 μM ruthenium were placed in vials.

Typical Purification Procedure

In a volumetric flask, 3 in methylene chloride (0.5 mL) was added to a solution of 2 (293 mg, 2.36 mmol) and triethylamine (657 μg, 4.72 mmol) in methylene chloride (1.5 mL) and stirred for 10 minutes. Water (approximately 2 mL) was added and the biphasic solution vigorously stirred for 15 minutes. The aqueous layer was separated and the methylene chloride removed in vacuo to isolate the product as a yellow oil.

ICP-MS Experiment

Samples of approximately 5 mg were precisely weighted on a microbalance, digested overnight with concentrated nitric acid, and diluted to 1% nitric acid. The samples were each measured 10 times and the intensities were obtained for ruthenium isotopes 99, 101, and 102. The intensity of pure 1% nitric acid was subtracted from the sample intensities to give the net intensities. To determine the actual concentration of ruthenium in the samples, the net intensitites were compared to that of ruthenium standards. The standards were obtained by diluting a ruthenium standard of 980 μg/mL Ru in 2 wt. % of HCl (obtained from Aldrich) with 1% nitric acid to get 2.04, 1.49, 0.98, 0.47, 0.1, 0.05, and 0.01 μg/mL Ru standards where each sample contained less than 0.01 wt. % HCl. The numbers given indicate the average amount of ruthenium obtained for the three isotopes measured.

What is claimed is:

1. A method of reducing a ruthenium complex from a first solution containing said complex by the addition of a second solution, comprising:
    adding a solubility-enhancing compound that enhances the solubility of said complex in the second solution;
    combining the first solution with the second solution wherein the second solution is immiscible with the first solution;
    mixing the first solution and second solution together; and,
    removing the second solution from the first solution;
    wherein the solubility-enhancing compound is a phosphine or derivative thereof.

2. The method as in claim 1 wherein the solubility-enhancing compound is selected from the group consisting of phosphines, sulfonated phosphines, phosphites, phosphinites, and phosphonites.

3. The method as in claim 1 further comprising adding an acid or a base prior to the mixing of the first solution and the second solution.

4. The method as in claim 2 wherein the solubility-enhancing compound is of the general formula $PR^1R^2R^3$
    wherein $R^1$, $R^2$, and $R^3$ are each independently selected from a group consisting of hydrogen, aryl, heteroaryl, $C_1$–$C_{10}$ alkyl, and cycloalkyl groups, each optionally substituted with one or more substituents selected from the group consisting of $C_1$–$C_5$ alkyl, $C_2$–$C_5$ alkenyl, $C_2$–$C_5$ alkynyl, allyl, aryl, heteroaryl and a functional group selected from the group consisting of alcohol, sulfonic acid, phosphine, phosphonate, phosphonic acid, thiol, ketone, aldehyde, ester, ether, amine, quaternary ammonium, imine, amide, imide, imido, nitro, carboxylic acid, disulfide, carbonate, isocyanate, carbodiimide, carboalkoxy, carbamate, acetal, ketal, boronate, cyanohydrin, hydrazone, oxime, oxazole, oxazoline, oxalane, hydrazide, enamine, sulfone, sulfide, sulfenyl, and halogen.

5. The method as in claim 4 wherein the solubility-enhancing compound is selected from the group consisting of $P(CH_2OH)_3$, $P(PhSO^3Na^+)$, $(CH_2OH)_2P$—$P(CH_2OH)_2$, $P(CyOH)_3$ $P(Cy)_3$, $PH(Cy)_2$, $P(Ph)_3$, and $P(R)_3$ wherein Ph is phenyl, Cy is cyclohexyl, and R is $C_1$–$C_5$ alkyl.

6. A method of reducing a ruthenium complex from a first solution containing said ruthenium complex by the addition of a second solution, comprising:
    adding a solubility-enhancing compound to the first solution that enhances the solubility of the ruthenium complex in the second solution;
    combining the first solution with the second solution wherein the second solution is immiscible with the first solution;

mixing the first and solution and second solution together; and, removing the second solution from the first solution;

wherein the solubility enhancing compound is a phosphine of the formula $PR^1R^2R^3$ wherein $R^1$, $R^2$, and $R^3$ are each independently selected from the group consisting of hydrogen, aryl, heteroaryl, $C_1$–$C_{10}$ alkyl, and cycloalkyl groups, each optionally substituted with one or more substituents selected from the group consisting of $C_1$–$C_5$ alkyl, $C_2$–$C_5$ alkenyl, $C_2$–$C_5$ akynyl, allyl, aryl, heteroaryl, and a functional group selected from the group consisting of alcohol, sulfonic acid, phosphine, phosphonate, phosphonic acid, thiol, ketone, aldehyde, ester, ether, amine, quaternary ammonium, imine, amide, imide, imido, nitro, carboxylic acid, disulfide, carbonate, isocyanate, carbodiimide, carboalkoxy, carbamate, acetal, ketal, boronate, cyanohydrin, hydrazone, oxime, oxazole, oxazoline, oxalane, hydrazide, enamine, sulfone, sulfide, sulfenyl, and halogen.

7. The method as in claim 6 further comprising adding an acid prior to the mixing of the first solution and the second solution.

8. The method as in claim 6 further comprising adding a base prior to the mixing of the first solution and the second solution.

9. The method as in claim 7 wherein the solubility-enhancing compound is selected from the group consisting of $P(CH_2OH)_3$, $P(PhSO^3Na^+)$, $(CH_2OH)_2P$—$P(CH_2OH)_2$, and $P(CyOH)_3$ wherein Cy is cyclohexyl.

10. The method as in claim 7 wherein the solubility-enhancing compound is selected from the group consisting of $P(Cy)_3$, $PH(Cy)_2$, $P(Ph)_3$, and $P(R)_3$ wherein Ph is phenyl, Cy is cyclohexyl, and R is $C_1$–$C_5$ alkyl.

11. A method of partially separating a ruthenium complex from a reaction product in a first solution by the addition of a second solution comprising:

adding a solubility-enhancing compound that enhances the solubility of the complex in the second solution;

combining the first solution with the second solution to form a mixture wherein the reaction product is insoluble in the second solution;

precipitating the reaction product from the mixture; and removing the reaction product precipitate from the mixture;

wherein the solubility-enhancing compound is a phosphine or derivative thereof.

12. The method as in claim 11 wherein the solubility-enhancing compound is selected from the group consisting of phosphines, sulfonated phosphines, phosphites, phosphinites, and phosphonites.

13. The method as in claim 11 wherein the solubility-enhancing compound is of the general formula $PR^1R^2R^3$ wherein $R^1$, $R^2$, and $R^3$ are each independently selected from a group consisting of hydrogen, aryl, heteroaryl, $C_1$–$C_{10}$ alkyl, and cycloalkyl groups, each optionally substituted with one or more substituents selected from the group consisting of $C_1$–$C_5$ alkyl, $C_2$–$C_5$ alkenyl, $C_2$–$C_5$ alkynyl, allyl, aryl, heteroaryl and a functional group selected from the group consisting of alcohol, sulfonic acid, phosphine, phosphonate, phosphonic acid, thiol, ketone, aldehyde, ester, ether, amine, quaternary ammonium, imine, amide, imide, imido, nitro, carboxylic acid, disulfide, carbonate, isocyanate, carbodiimide, carboalkoxy, carbamate, acetal, ketal, boronate, cyanohydrin, hydrazone, oxime, oxazole, oxazoline, oxalane, hydrazide, enamine, sulfone, sulfide, sulfenyl, and halogen.

14. The method as in claim 11 wherein the solubility-enhancing compound is selected from the group consisting of $P(CH_2OH)_3$, $P(PhSO^3Na^+)$, $(CH_2OH)_2P$—$P(CH_2OH)_2$, $P(CyOH)_3$ $P(Cy)_3$, $PH(Cy)_2$, $P(Ph)_3$, and $P(R)_3$ wherein Ph is phenyl, Cy is cyclohexyl, and R is $C_1$–$C_5$ alkyl.

15. The method as in claim 11 wherein the solubility-enhancing compound is $P(CH_2OH)_3$.

16. A method of partially separating a ruthenium complex from a reaction product in a reaction mixture, comprising:

adding a solubility-enhancing compound to the mixture wherein the solubility-enhancing compound is of the general formula $PR^1R^2R^3$ wherein $R^1$, $R^2$, and $R^3$ are each independently selected from the group consisting of hydrogen, aryl, heteroaryl, $C_1$–$C_{10}$ alkyl, and cycloalkyl groups, each optionally substituted with one or more substituents selected from the group consisting of $C_1$–$C_5$ alkyl, $C_2$–$C_5$ alkenyl, $C_2$–$C_5$ alkynyl, allyl, aryl, heteroaryl, and a functional group selected from the group consisting of alcohol, sulfonic acid, phosphine, phosphonate, phosphonic acid, thiol, ketone, aldehyde, ester, ether, amine, quaternary ammonium, imine, amide, imide, imido, nitro, carboxylic acid, disulfide, carbonate, isocyanate, carbodiimide, carboalkoxy, carbamate, acetal, ketal, boronate, cyanohydrin, hydrazone, oxime, oxazole, oxazoline, oxalane, hydrazide, enamine, sulfone, sulfide, sulfenyl, and halogen;

adding silica gel to the reaction mixture; and removing the silica gel from the reaction mixture.

17. The method as in claim 16 further comprising adding an acid or a base prior to the addition of the silica gel to the reaction mixture.

18. The method as in claim 16 wherein the solubility-enhancing compound is selected from the group consisting of $P(CH_2OH)_3$, $P(PhSO^3Na^+)$, $(CH_2OH)_2P$—$P(CH_2OH)_2$, and $P(CyOH)_3$ wherein Cy is cyclohexyl.

19. The method as in claim 16 wherein the solubility-enhancing compound is $P(CH_2OH)_3$ and the method further comprises adding triethylamine to the reaction mixture prior to the addition of the silica gel.

20. A method of increasing the solubility of a ruthenium complex in a solution, comprising:

adding a solubility-enhancing compound to the solution, wherein the solubility-enhancing compound is a phosphine or derivative thereof.

21. The method as in claim 20 wherein the solubility-enhancing compound increases the solubility of the ruthenium complex in the solution such that the solution is analyzable using inductively coupled plasma mass spectroscopy.

22. The method as in claim 20 wherein the solubility-enhancing compound is selected from the group consisting of phosphines, sulfonated phosphines, phosphites, phosphinites, and phosphonites.

23. The method as in claim 20 wherein the solubility-enhancing compound is of the general formula $PR^1R^2R^3$ wherein $R^1$, $R^2$, and $R^3$ are each independently selected from a group consisting of hydrogen, aryl, heteroaryl, $C_1$–$C_{10}$ alkyl, and cycloalkyl groups, each optionally substituted with one or more substituents selected from the group consisting of $C_1$–$C_5$ alkyl, $C_2$–$C_5$ alkenyl, $C_2$–$C_5$ alkynyl, allyl, aryl, heteroaryl and a functional group selected from the group consisting of alcohol, sulfonic acid, phosphine, phosphonate, phosphonic acid, thiol, ketone, aldehyde, ester, ether, amine, quaternary ammonium, imine, amide, imide, imido, nitro, carboxylic acid, disulfide, carbonate, isocyanate, carbodiimide, carboalkoxy, carbamate, acetal, ketal, boronate, cyanohydrin, hydrazone, oxime, oxazole, oxazoline, oxalane, hydrazide, enamine, sulfone, sulfide, sulfenyl, and halogen.

24. The method as in claim 20 wherein the solubility-enhancing compound is selected from the group consisting of $P(CH_2OH)_3$, $P(phSO_3Na^+)$, $(CH_2OH)_2P-P(CH_2OH)_2$, $P(CyOH)_3$, $P(Cy)_3$, $PH(Cy)_2$, $P(Ph)_3$, wherein Ph is phenyl, Cy is cyclohexyl, and R is $C_1-C_5$ alkyl.

25. The method as in 20 further comprising the addition of an acid or a base.

26. The method as in claim 25 wherein the base is triethylamine and wherein the solubility-enhancing compound is $P(CH_2OH)_3$.

* * * * *

UNITED STATES PATENT AND TRADEMARK OFFICE
CERTIFICATE OF CORRECTION

PATENT NO. : 6,376,690 B1
DATED : April 23, 2002
INVENTOR(S) : Robert H. Grubbs et al.

It is certified that error appears in the above-identified patent and that said Letters Patent is hereby corrected as shown below:

Title page,
Item [73], Assignee, should read
-- [73] Assignee: California Institute of Technology, Pasadena, CA (US) --.

Signed and Sealed this

Twenty-fifth Day of January, 2005

JON W. DUDAS
*Director of the United States Patent and Trademark Office*